US006343507B1

(12) United States Patent
Felling et al.

(10) Patent No.: US 6,343,507 B1
(45) Date of Patent: Feb. 5, 2002

(54) METHOD TO IMPROVE THE QUALITY OF A FORMATION FLUID SAMPLE

(75) Inventors: Michelle M. Felling, Houston; Charles W. Morris, The Woodlands; Robert J. Butsch, Tomball, all of TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/468,013

(22) Filed: Dec. 20, 1999

Related U.S. Application Data

(63) Continuation-in-part of application No. 09/126,513, filed on Jul. 30, 1998.

(51) Int. Cl.[7] .......................... G01N 22/04; G01F 5/00; G06F 19/00; G01V 3/30
(52) U.S. Cl. .................. 73/152.19; 73/152.31; 73/152.24; 73/152.28; 73/152.55; 73/61.41; 166/254.2; 175/5; 702/12; 250/255
(58) Field of Search ............ 73/152.19, 152.24–152.27, 73/152.28, 152.42, 152.55, 61.43–61.41, 61.61, 152.31, 152.59, 152.22; 166/250.07, 254.2; 175/48, 50; 702/12; 250/255–256

(56) References Cited

U.S. PATENT DOCUMENTS

| | | | | |
|---|---|---|---|---|
| 4,535,843 A | * | 8/1985 | Jageler ........................ | 166/250 |
| 4,994,671 A | * | 2/1991 | Sabinya et al. .............. | 250/255 |
| 5,201,220 A | * | 4/1993 | Mullins et al. ............... | 73/155 |
| 5,266,800 A | * | 11/1993 | Mullins ....................... | 250/256 |
| 5,331,156 A | * | 7/1994 | Hines et al. ................. | 250/256 |
| 5,341,100 A | * | 8/1994 | Taylor ......................... | 324/341 |
| 5,351,532 A | * | 10/1994 | Hager ......................... | 73/153 |
| 5,644,244 A | * | 7/1997 | Marrelli et al. .............. | 324/637 |
| 5,741,962 A | * | 4/1998 | Birchaki et al. .......... | 73/152.16 |
| 5,803,186 A | * | 9/1998 | Berger et al. ................. | 175/50 |
| 5,859,430 A | * | 1/1999 | Mullins et al. .............. | 250/255 |
| 5,926,024 A | * | 7/1999 | Blount et al. ................ | 324/324 |
| 6,157,893 A | * | 12/2000 | Berger et al. .................. | 702/9 |

* cited by examiner

Primary Examiner—Hezron Williams
Assistant Examiner—David J. Wiggins
(74) Attorney, Agent, or Firm—John J. Ryberg; Steven L. Christian; JL (Jennie) Salazar

(57) ABSTRACT

The present invention provides a method for improving the quality of a formation fluid sample by taking the sample at a time when the formation fluid composition contains the most favorable portion of hydrocarbons. This task is accomplished by determining in real-time, the composition of the fluid flowing into a downhole tool from the formation. This method determines the optical density of the fluid as the fluid flows through the tool. An optical density spectrum is generated from the optical density measurement. The optical density spectrum is compared to a composite optical density spectrum generated from a database of known fluid samples. As a result of the comparisons, there is a determination of the derivations between corresponding features of the two spectra. Adjustments are made to the components of the composite spectrum until the deviations between the two spectra are at an acceptable minimum. Determinations of the fluid composition are made from the composition of the composite spectrum at the minimum deviation. The sampling process begins when the fluid composition has a desirable fractional component of hydrocarbons in the fluid.

32 Claims, 11 Drawing Sheets

METHOD TO IMPROVE THE QUALITY OF A FORMATION FLUID SAMPLE

CROSS-REFERENCE TO RELATED APPLICATION

This application is a continuation-in-part of U.S. patent application Ser. No. 09/126,513, filed on Jul. 30, 1998.

FIELD OF THE INVENTION

This invention relates to a method for improving the quality of a formation fluid sample. In particular, the invention relates to a real-time method for determining the composition of a formation fluid and/or differentiating between oil-base filtrates and formation fluid hydrocarbons during the process of pumping fluids from a downhole formation for the purpose of taking a formation fluid sample.

BACKGROUND OF THE INVENTION

It is desirable to evaluate formation fluids that may indicate the existence and/or type of subsurface hydrocarbon fluid reservoirs. To assist in this evaluation, wireline formation tester tools are commonly used during openhole logging operations to recover formation fluid samples and to determine the type and distribution of formation fluids. Methods of positive fluid type identification usually come from inspection and/or analysis of recovered samples at the surface. As a result of these methods there are long-standing difficulties associated with wireline fluid sampling operations such as: mud filtrate invasion into the formation fluid, establishing and maintaining a seal between the tool probe and the borehole wall, and drawing down the pressure of the formation fluid below saturation pressure. These and other issues are addressed by downhole tools such as the tool described in U.S. Pat. Nos. 4,860,581 and 4,936,139 issued to Zimmerman et al.

The Zimmerman patents disclose a downhole tool that can take formation fluid samples and determine formation properties from these samples. These downhole wireline tools may be modularly constructed so that a tool can perform multiple tasks in a single descent of the tool into the borehole. FIG. 1 shows such a downhole tool. This tool 1 has a probe module 2 that establishes fluid communication between the tool and the earth formation 3 via a probe 4. This tool contains a pump out module 5 for pumping fluid from the formation into the tool and a module 6 to analyze fluid from the earth formation.

FIG. 1 illustrates the problems associated with taking a formation fluid sample. The formation 3 contains a mixture of both the desired hydrocarbon type fluid 7 and the undesired contaminated fluid filtrates 8. The less contaminated hydrocarbon fluid is often referred to as the 'clean fluid'. The borehole annulus 9 also contains contaminated filtrates. Contaminated formation fluid 8 is in closer proximity to the borehole and a greater portion of that fluid is initially in the mixture. During the pump out process, the composition of this mixture will continually change until the composition begins to stabilize. From the fluid analyzer 6, it is determined when the composition of the fluid begins to stabilize. Once fluid stabilization has occurred, and depending on the portion of hydrocarbon in the mixture, the incoming fluid may be diverted into the sample chamber 10. However, during any attempt to retrieve the clean fluid, it will be necessary to pump out the contaminated formation fluids before getting to the desired clean formation fluid.

In addition to the mixture of contaminated and clean fluids, other factors can affect the fluid sample quality. These factors include the rock properties, the mud filtrate invasion volume, the pressure differential used to produce the fluid, and the clean up time. The rock properties usually cannot be modified, but selection of the sample interval can alter the influence of the vertical permeability in some cases. The fluid flow geometry into a probe 4, even under stable conditions, can include a significant vertical component from the borehole-invaded zone that contains mud filtrate contamination. Sample points taken near vertical flow barriers can reduce the influx of mud filtrate into the probe.

Drilling operations to create the borehole require various types of drilling muds. The use of oil-based drilling mud systems causes major problems in wireline logging including problems during attempts to obtain high quality fluid samples. These mud filtrate fluids are mixed in the formation oil. Therefore, quantification of the oil-base material in the formation oil becomes difficult without laboratory analysis. The presence of even small volumes of oil-base filtrate in the sample can significantly alter the pressure-volume-temperature (PVT) properties of formation oil. Generally, the additives in the filtrate change the character of the optical density response curves of the oil-based mud filtrate. This change affects the optical analysis of the filtrate and increases the difficulty of distinguishing an oil-based filtrate from a formation hydrocarbon fluid. Because of this difficulty in making this distinction, the quality of a fluid sample may be unreliable.

One conventional sample taking method that addresses this problem is to pump fluid from the formation through the tool for a predetermined period of time or a predetermined pumped volume of fluid. It is assumed that after this period, the fluid passing though the tool should be at an acceptable contamination level. Although using empirical models or reservoir simulators to estimate the time required to obtain an acceptable fluid sample is appealing in concept, it requires significant knowledge of the formation rock properties, formation fluids, mud filtrate, mud cake, formation damage zone, flow patterns, and other information in the near wellbore zone which is not available.

A second approach is explained using the tool in FIG. 1. A downhole tool 1 is suspended in a borehole 9 from a wireline 11 or drill pipe. In this method, a probe 4 in fluid communication with the tool body is also in contact with the borehole wall 12. To retrieve the formation fluid, a pressure drop is created in the tool across the probe. This pressure drop causes formation fluid to flow from the high-pressure formation to the lower pressure probe and into the tool. The pumpout module 5 is used to draw fluids from the formation, through the tool flowline 13 and out into the borehole (if desired). As fluids pass through the tool, the probe module measures their resistivity and temperature and the optical fluid analyzer (OFA) 6 measures their optical properties (i.e. fluid density).

Optical data are processed in real-time to quantitatively determine flowing oil and water fractions, and to obtain a qualitative indication of the amount of free gas in the flow system. Optical fluid responses vary for different materials. As shown in FIG. 2, there are significant differences between water and oils. The responses of water 14 and oils 15 and 16 show these differences When the fluid analysis begins to show stabilization, a fluid sample is taken by diverting fluid into a sample chamber.

A flowline 13 passes though two independent optical sensors in the OFA module 6. In one sensor, absorption spectroscopy is used to detect and analyze liquid. In the other sensor, a special type of optical reflection measurement detects gas. These detections allow wellsite personnel to decide whether to divert the fluid flow into a sample chamber for retrieval, to continue to expel the fluid into the borehole or to a dump chamber, or to increase the sampling pressure above bubblepoint. This module can also verify that the formation contains only water or only gas and/or that a sample is not necessary. Thus, the sample chambers in the tool are kept available only for desired fluids. After a decision has been made to switch from pumpout mode to sampling mode, the OFA module continues to monitor the fluid in the flowline, particularly to verify that production remains above bubblepoint.

As stated, the OFA module has a visible and near-infrared absorption spectrometer for oil/water discrimination and a refractometer for free gas identification. Each OFA sensor responds to one of two basic optical properties, namely absorption and index refraction. These properties are measured by passing light through a window opening onto the flowline. The measured absorption spectra depend on the composition of the sampled fluid. FIG. 2 shows OFA responses of different formation materials in terms of optical density. Optical density is defined as the logarithm of the inverse of light transmittance for several fluids. The optical responses are a plot of the optical density of the material versus wavelength ranges. FIG. 2 shows standard responses for water 14, light oil 15 and heavy oil 16. Notice that water 14 and oils 15 and 16 respectively have considerably different light absorption in the near-infrared region (approximately 700 nm–2400 nm). Water has an absorption peak at 1450 nanometers (nm); the oils have an absorption peak at about 1720 nm. This difference makes it possible to readily distinguish between water and oil in the OFA. Condensates 17 and oil-based filtrates 18 have absorption peaks that are similar to the oils. The distinction between oils and filtrates is not as clearly defined.

Another important feature of the OFA is the ability to differentiate between light and heavy oils by identifying wavelengths of the responses. Hydrocarbons typically have shorter wavelengths and are absorbed before longer wavelengths of water. The selective absorption of wavelengths results from the proportion of complex molecules, such as asphaltenes, present in the oil. As the proportion of heavier hydrocarbon molecule chains increase, more of the shorter wavelengths are absorbed.

A requirement to insure the recovery of quality fluid samples is a detection system capable of indicating fluid types in addition to water and oil. The sensor in the probe module 2 generally performs this identification function by providing a resistivity measurement over a wide range fluids. However, some conditions, and particularly wells drilled with oil-base mud (OBM), may require more optical fluid analysis from the OFA module to determine the additional fluid types. This module can use optical analysis techniques to identify the various fluids in the flowline of the tool.

Although the above methods attempt to address the problem of obtaining a cleaner formation fluid sample by identifying whether water and oil are present in a fluid, these methods do not address the problem of identifying the type of fluid in the sample or the percentage of each type of fluid in the sample. One discussion of solutions to this problem was presented in SPE Paper No. 39093, published in October 1997. This solution used a database of responses along with other formation data to simulate flow rates and give an estimate of the pumpout time needed to obtain an acceptable fluid sample. In addition, this method requires certain data regarding the downhole conditions of the formation, such as API gravity and density, which is not initially available.

There remains a need for a technique that can determine in real-time the composition of formation fluid flowing through a downhole tool during a sample-taking operation. There also remains a need for a technique that determines the relative amounts of the fluids in the sample in order to determine whether there is an acceptable level of the desirable formation fluid in the sample.

SUMMARY OF THE INVENTION

It is an objective of this invention to provide a reliable and real-time method for improving the quality of a formation fluid sample taken downhole.

Another objective of this invention is to determine the composition of hydrocarbons, waters, highly absorbing fluids and downhole filtrates in the formation fluids.

Another objective of this invention is to monitor in real-time the formation fluid flowing into a downhole tester tool in order to determine the appropriate time to take the fluid sample.

A fourth objective of this invention is to differentiate between oil-based fluid filtrates and formation hydrocarbon fluids.

Another objective of this invention is to distinguish between light hydrocarbon fluids and heavy hydrocarbon fluids.

Another objective of this invention is to use fluid characteristic curves to quantitatively describe the formation fluid.

Another objective of this invention is to use fluid optical density to determine fluid activity.

The present invention provides a technique to determine in real-time, the composition of fluid being pumped into a downhole tester tool. This technique determines the relative portion of hydrocarbons (oil), water, filtrates and solids in the formation fluid flowing into the tool during the sample taking process. Since this fluid composition changes, the objective is to monitor the composition of the fluid flowing into the tool until the fluid composition contains an acceptable portion of the desired formation hydrocarbon fluid or until a decision is made not to take a fluid sample at that location. Once there is an acceptable level of hydrocarbon fluid flowing into the tool, the fluid flow into the tool is diverted into a sample chamber to collect a sample of the fluid.

This invention can use an optical fluid analyzer (OFA) in a downhole tester tool to analyze the incoming fluid. As previously described the OFA monitors the fluid in the flowline using a sensor system (an optical spectrometer and an optical gas detector) closely spaced along the tool flowline. The OFA produces an optical spectrum (response) measured across a plurality of wavelength channels in the OFA. The different channels contain detectors that detect various light wavelengths transmitted through the OFA.

In the method of this invention, the OFA produces a measured absorption spectrum (log), of the inflowing fluid from the wavelengths detected at the various channels of the OFA. This spectrum is a combination of optical fluid responses representing hydrocarbons, water, solids and filtrates that compose the formation fluid, forming an array of the components of an optical emission passing through the formation fluid, separated and arranged according to wavelength. The present invention determines the composition of the measured absorbed light spectrum, and thereby which materials are present in the fluid and the portions of each material in the fluid. A premise of this invention is that the measured spectrum is the sum (i.e. linear, non-linear) of the various fluid responses.

The formation fluid composition is determined by comparing the measured spectrum to a composite spectrum of known responses for standard formation fluid materials. The present invention uses a database of optical density fluid responses from various fluid and gas materials to aid in the determination of the composite spectrum. The composite spectrum is generated from responses selected from the optical density fluid response database. The selected responses are combined to produce a composite spectrum. This composition spectrum is an estimation of the materials in the formation fluid.

A spectral fitting procedure is performed on the measured spectrum using the composite spectrum of database responses to determine the types of materials in the measured spectrum. During this fitting procedure, corresponding features of the composite spectrum are compared to features of the measured spectrum to determine the derivation between the two spectra. If the deviation between the two spectra is within an acceptable level, there is a best fit between the spectra. The composite spectrum is then used to determine the formation fluid composition. If this deviation is not acceptable, changes are then made in the fractional components of the composite spectrum using a weighted linear regression technique until the composite spectrum matches/fits the measured spectrum. After there is an acceptable match between the measured absorption spectrum and the composite spectrum, a determination is made from the resulting composite spectrum of the types and portions of each material in the fluid.

DETAILED DESCRIPTION OF THE INVENTION

This invention determines the relative portions of oil, water, mud filtrate, and solids in a fluid flowing into a downhole tool by using a measured optical density spectrum to determine components of the fluid. The spectrum is a 10-channel waveform of the optical density versus light wavelengths. This measured optical spectrum is compared to a composite spectrum of known responses for oil, water, mud filtrate, and solids and a determination of the respective fluid portions of the fluid is made. These relative portions are determined by a weighted linear regression of the measured spectrum against the multiple components of the composite spectrum of known responses across all wavelengths. The multiple components in the formation fluid are water, mud, filtrate, solids, and one or more oils. The optical responses of a number of different oils, waters, mud filtrates and mud systems (components and mixtures thereof) have been characterized and are available for selection from a fluid response database. An option is given to use one or two oils in the composite spectrum.

Figure 1:
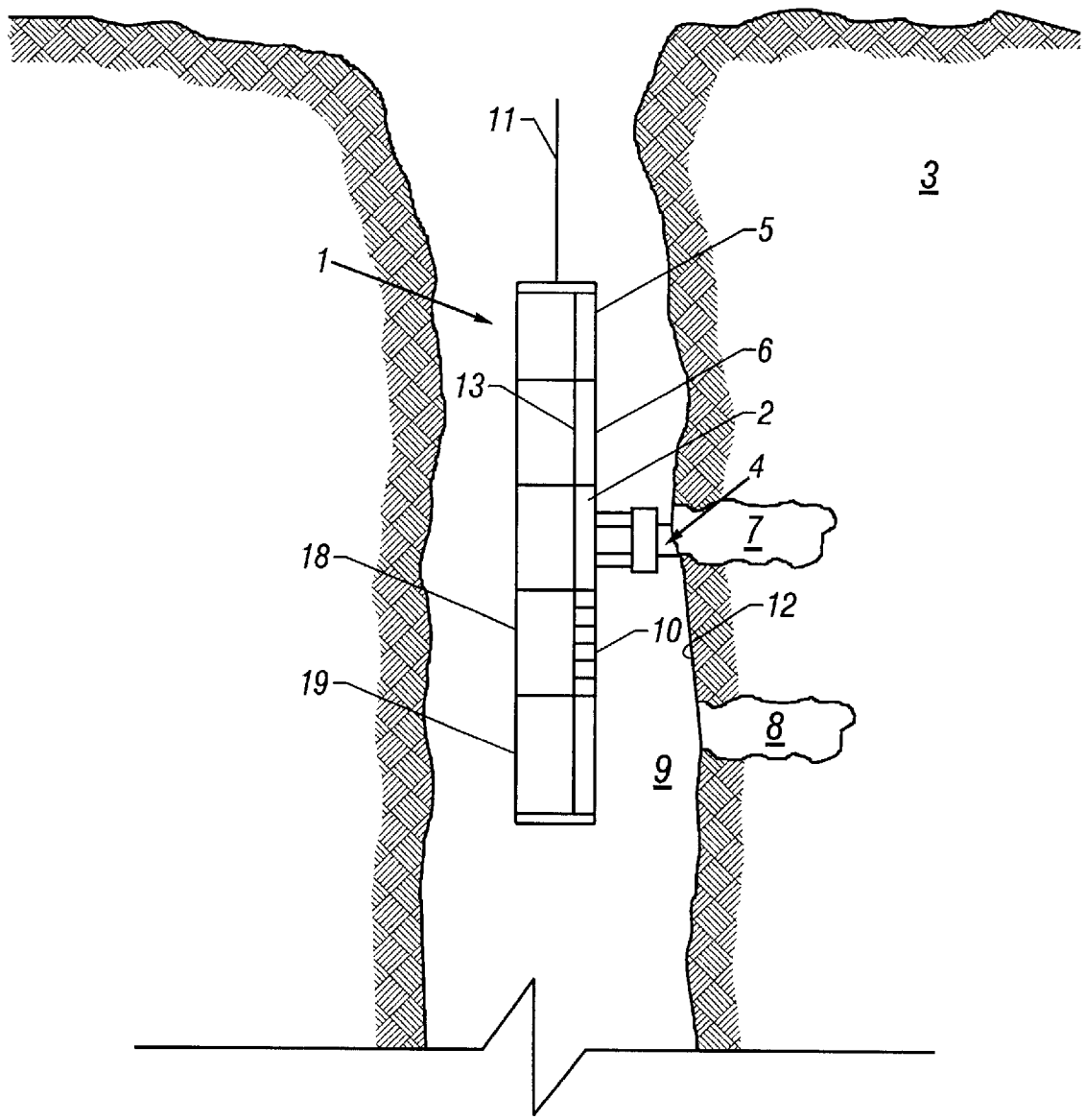
FIG. 1 is a diagram of a formation tester tool suspended in an earth formation, said formation having hydrocarbon fluid and filtrates.

This description of the present invention is implemented using a downhole tester tool such as the Modular Formation Dynamics Tester (MT) tool described in the previously mentioned Zimmerman patents. However, a form of this technique could be implemented with other downhole tool systems such as Drill-Stem Test (DST), Tough Logging Condition (TLC), Logging-While-Drilling (LWD), and Measurement-While-Drilling (MWD) systems. The MDT tool shown in FIG. 1 consists of several modules that perform various functions. Some of these modules include pumpout module 5, fluid analysis module 6, probe module 2, sample chamber module 18 and packer module 19. The measured spectrum is generated through optical analysis of the fluid flowing into the tester tool. The placement of the fluid analysis module or OFA 6 in the tester tool is usually between the probe module 2 and the sample chamber module 18 or pumpout module 5, but the OFA can be placed at any number of places in the tool.

The OFA utilizes a visible and near infrared absorption spectrometer for fluid discrimination and a refractometer for free gas. The spectrometer measures the transmittance of a liquid at 10 different wavelength channels and distinguishes between oil and water by comparing the resulting absorption spectra in the visible and near-infrared region. Each channel represents a different wavelength range. The spectrometer yields quantitative data on fluid phase volumes and qualitative data concerning fluid coloration. A detailed description of the OFA and examples of its operations are disclosed in U.S. Pat. No. 5,331,156 to Hines, et. al., U.S. Pat. No. 5,266,800 to Mullins, U.S. Pat. No. 5,201,220 to Mullins, et. al., and U.S. Pat. No. 5,167,149 to Mullins, et. al. All of the above mentioned patents are assigned to the assignee of the present application, and are as well incorporated herein by reference.

Figure 2:
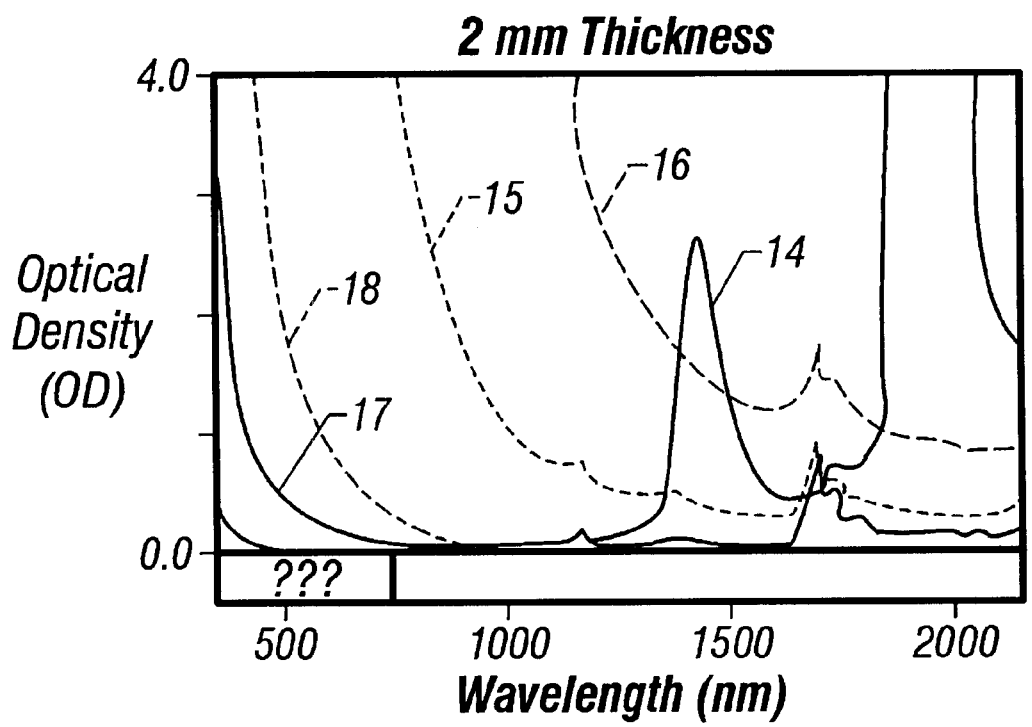
FIG. 2 is a plot of standard optical responses for typical formation fluids.

The OFA monitors the fluid flow in the flowline using two sensors closely spaced along the flowline. Optical fluid identification measurements are based on the considerably different fight absorption spectra of water and oil in the near infrared region. As previously discussed and referring to FIG. 2, water 14 has an absorption peak at 1450 nm and an absorption region at 2000 nm, and oils 15, 16 both have absorption peaks at 1720 nm. The condensates 17 and filtrates 18 have absorption peaks similar to that of the oils. Passing light through a window opening onto the flowline 13 (see FIG. 1) performs the measurements in the OFA. The transmitted light is received through a second window at the opposite side of the tool, then separated into a measured spectrum by an array of filters and detectors. The transmitted light intensity at 10 wavelengths across the visible and near infrared range is recorded. The resulting generated or measured spectrum depends on the composition of the analyzed fluid. The longer wavelength part of the spectrum reveals information about the relative concentrations of the basic constituents (oil or water). The other region from the visible to near infrared wavelengths is used to differentiate various types of oils and water.

This invention uses spectral analysis techniques in determining the composition of formation fluids. In the basic technique for performing spectral analysis in this invention, a measured or detected spectrum for a formation fluid of unknown composition is compared with a composite spectrum comprised of weighted standard spectra representing the likely materials present in the formation fluid. The weighted coefficients for the standard spectra, which give the best fit of the composite standard spectrum to the measured spectrum, as determined for example by the regression analysis, represent the relative proportions of the materials in the formation fluid. The minimum deviation between the measured and the composite (fitted) spectrum define the best fit. One common best-fit method is to determine statistically the weighted average square deviation between the measured and the fitted spectrum. In order to improve the fit (alignment) between the measured and a composite spectrum comprising the plurality of standard spectra, the standard spectra are adjusted by selecting different known fluid responses to compensate for differences between the spectral resolution of the measured spectrum and the spectral resolution associated with the standard spectrum.

Figure 3:
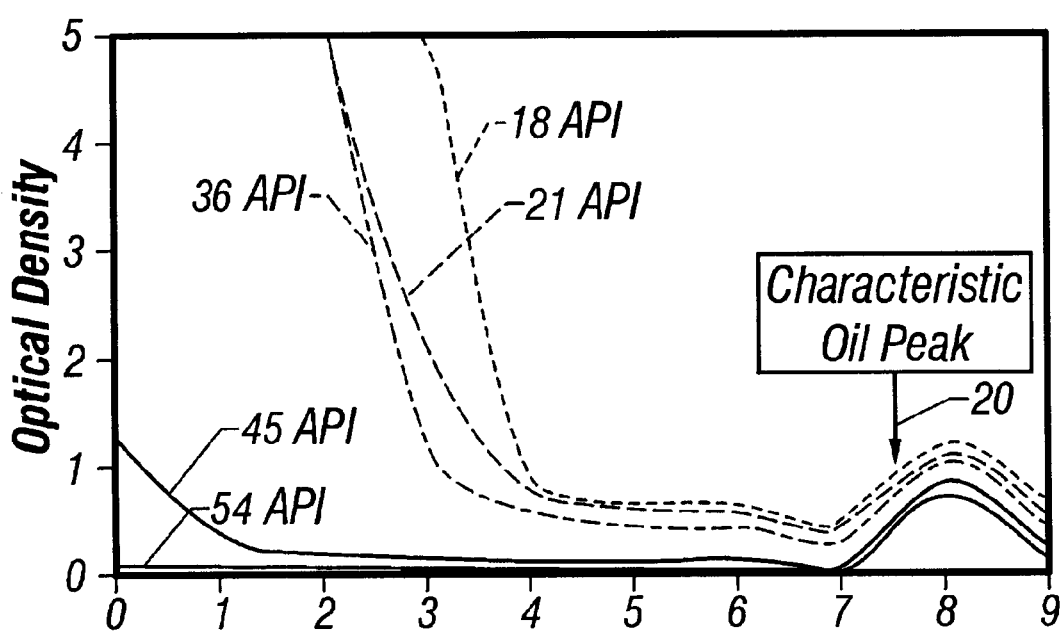
FIG. 3 is a plot of an optical response of typical hydrocarbon fluids found in an earth formation.

To generate the composite standard spectrum, a sample evaluation was initiated to characterize optical density responses for a variety of fluid systems. Tests were performed using oilfield hydrocarbons, formation waters, drilling muds, mud filtrates, synthetic oil-base fluids and other mixtures thereof. The responses for these materials were compiled and stored in a database. Some of these spectra will be discussed in this description. Using this database, optical density measurements can do an excellent job of differentiating between oil and water. Hydrocarbon responses also show a strong correlation trend with the optical fluid density measurements and can be used to estimate the in situ oil gravity. Furthermore, differentiation between oil base drilling fluid filtrates and hydrocarbons is also possible. The response database includes approximately twenty crude oils of API gravity ranging from 60° to 18°. FIG. 3 shows OFA reference responses for five of the oils (between 54° and 18° API). In FIG. 3, the characteristic oil peak 20 appears on OFA channel 8. A strong correlation was found between API gravity (fluid density) and optical density (absorption) in all the spectrometer channels. For high gravity oils (above 50°), the optical density on all wavelength channels (except channel 8) was low, being less than 0.2. As API gravity decreased higher optical densities were seen in the lower channels, increasing up to the maximum calibrated optical density value of 5. Eventually, with low gravity oils (18°–30° API) there was complete absorption on channels 0 to 3. For the majority of hydrocarbon liquids studied, it was observed that there is a range of wavelengths (from 700 to 1600 nm) as detected by OFA channels 3–7 where the optical density is essentially constant. A useful real-time output from the OFA was the fluid coloration indicator. When the API gravity was high, larger than 50°, the coloration indicator is of the order of $10^{-6}$, indicating little light attenuation. The coloration curve increased in magnitude, up to approximately $10^{-2}$, as the API gravity decreased. This information concerning optical density was important in distinguishing between light and heavy hydrocarbons.

Figure 4:
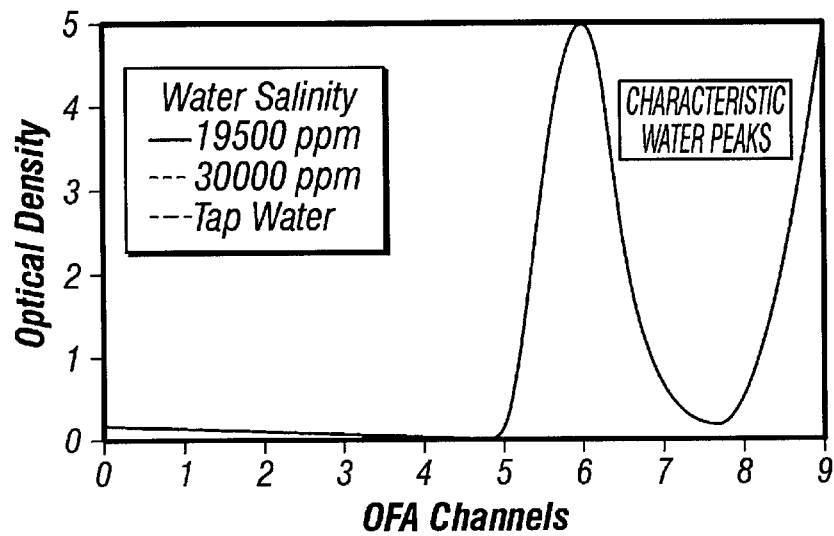
FIG. 4 is a plot of an optical density response for formation waters in an earth formation.

FIG. 4 presents water responses of different salinities together with a response of tap water given as a reference. It is seen that water displays its characteristic peaks in OFA channels 6 and 9. Results from experiments suggest that the optical density response for water does in fact depend slightly on salinity. However, the characteristic channels 6 and 9 always peak at the maximum optical density value regardless of salinity.

Figure 5:
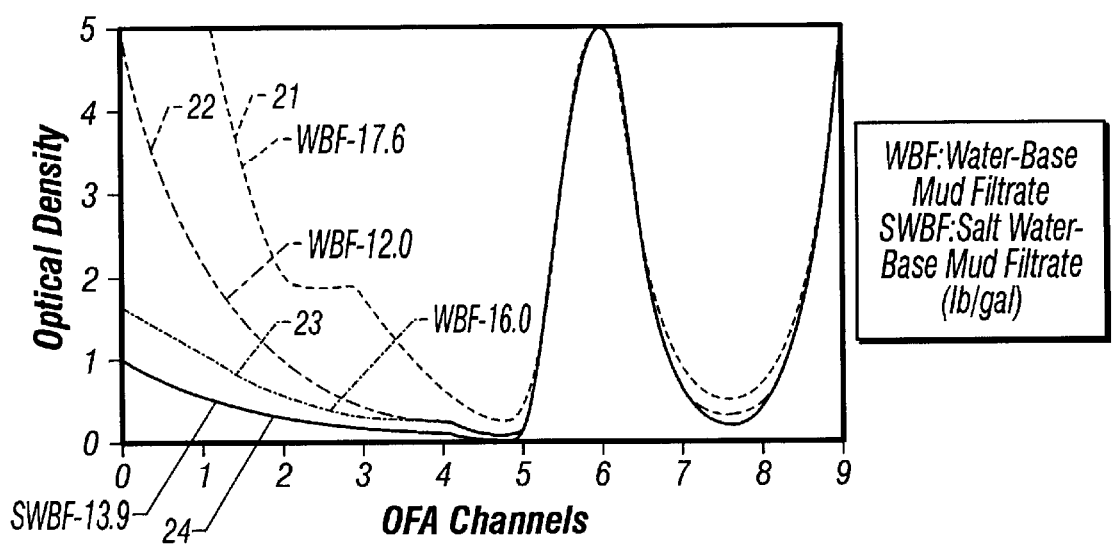
FIG. 5 is a plot of an optical density response for various water-based mud filtrates.

FIG. 5 presents OFA results from three water-based mud filtrates (WBF) 21, 22 and 23 and one salt water-base filtrate 24 (SWBF) sample. Optical density peaks on channels 6 and 9, as previously seen in FIG. 4, for all responses. The salt water-base filtrate showed a slight baseline decrease in optical density in channels 7 and 8 compared to the fresher water-base filtrates; the more saline filtrate also displayed a slightly lower optical density on most channels. There appears to be a slight dependence of optical density upon mud weight, which varied from 9.5 lb/gal to 17.6 lb/gal. In general, filtrate coloration increased as mud weight increased. There is also a correlation between optical density and viscosity.

Figure 6:
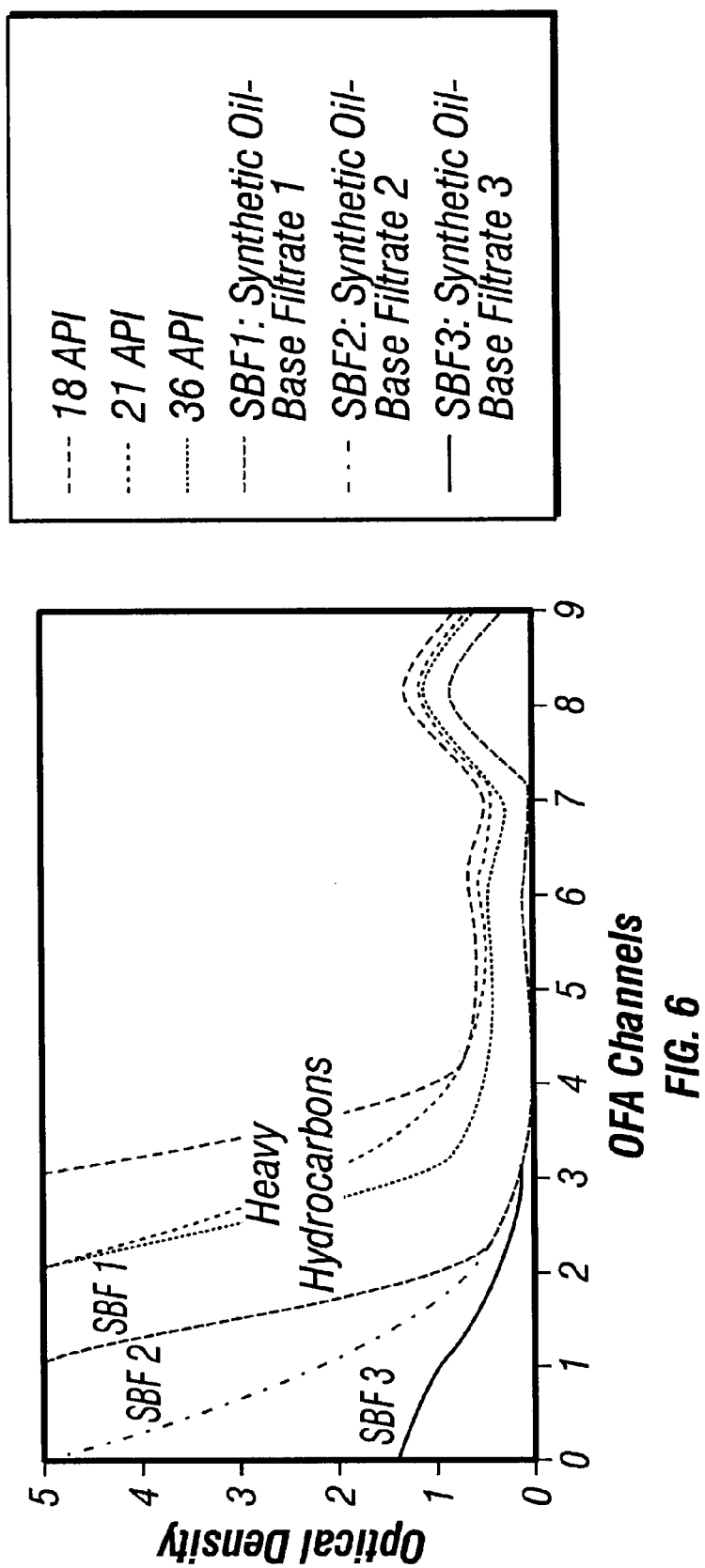
FIG. 6 is a plot of an optical density response for synthetic filtrates and heavier hydrocarbons.

FIG. 6 shows the OFA responses for several commercially available synthetic oilbase mud filtrates. Selected hydrocarbon responses (from FIG. 3) are overlain for comparison. Various synthetic filtrates were examined, and all the samples responded with an optical density peak on channel 8, which is characteristic of oil. Three of the five filtrates were found to be very similar, exhibiting very low optical density values for all channels except channel 8. OFA fluid coloration output (FCOL) was very low.

A clear, light to medium brown mineral oil-base mud filtrate sample was also analyzed with the OFA (results are not shown). Very low optical density values were observed on all channels, except for the characteristic oil peak in channel 8. Fluid coloration (FCOL) was approximately $3 \times 10^6$. The response was found to be very close to the clear synthetic oil-base filtrate responses.

Figure 7:
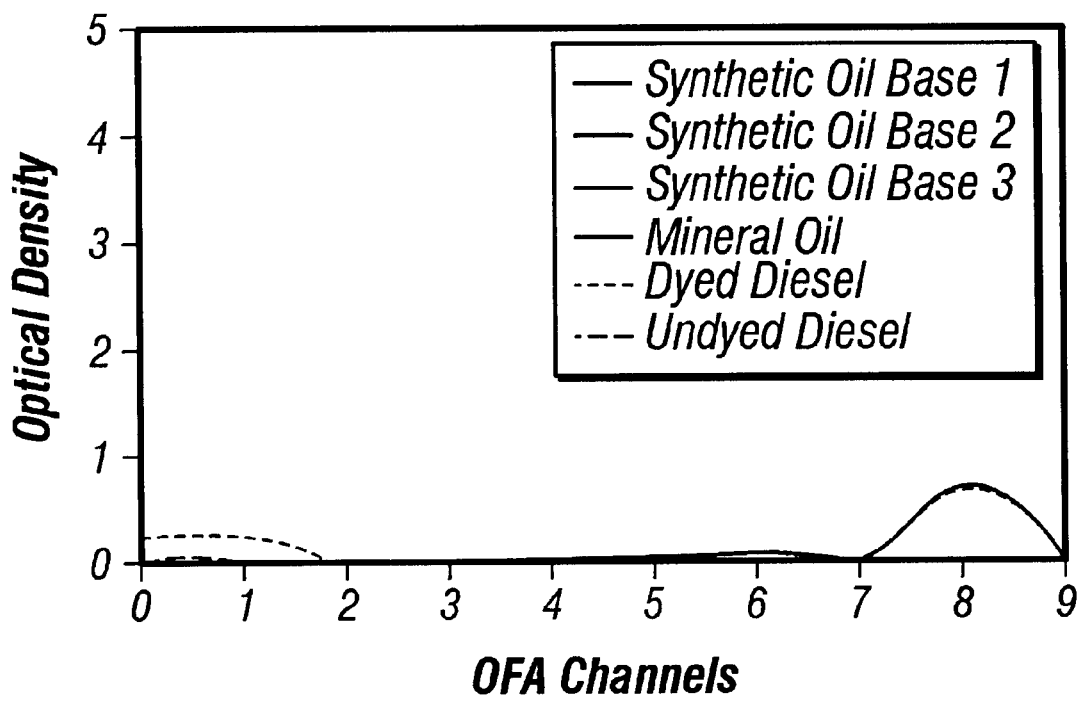
FIG. 7 is a plot of an optical density response for various oil-base drilling muds.

Samples of typical drilling muds were also obtained and examined with the OFA; these fluids contained no additives or drilling debris. Responses from the six different synthetic oil-base muds that were analyzed are shown in FIG. 7. All samples displayed similar behavior. The measured optical density was very small for all channels except for the characteristic oil peak on channel 8. Essentially these muds behaved as clear liquids; their responses were similar to that of a hydrocarbon of high API gravity (>50°). Differences in the character of the optical density curves between FIGS. 6 and 7 (filtrate and mud) are due to additives in the filtrates, which influence OFA measurements in the lower numbered channels. This comparison emphasizes the fact that to obtain the best results from the OFA, wellsite filtrate samples should always be used for comparative purposes during MDT sampling operations.

Emulsifier was added incrementally to one of the synthetic oil-base muds to examine the OFA response (results are not reproduced). Up to 2% emulsifier was used since this was consistent with field practice. As emulsifier was added, the measured optical density increased very slightly in lower wavelengths (signaling addition of color to the mixture); only channels 0 and 1 were affected. A similar response was observed when emulsifier was incrementally added to the dyed diesel mud.

Mixtures of hydrocarbons and synthetic oil-base muds were prepared in known quantities in order to measure the optical density. The test was repeated for three different hydrocarbons of API gravity 54°, 41° and 32°.

There was little difference in the optical density response after mixing the 54° API oil (not shown) with varying quantities of mud. Optical density channels 0 and 1 showed a slight increase with decreasing amounts of mud. The hydrocarbon was a light, clear yellow and the mud a pale, clear yellow; the mixture showed no discernible change in color.

Figure 8:
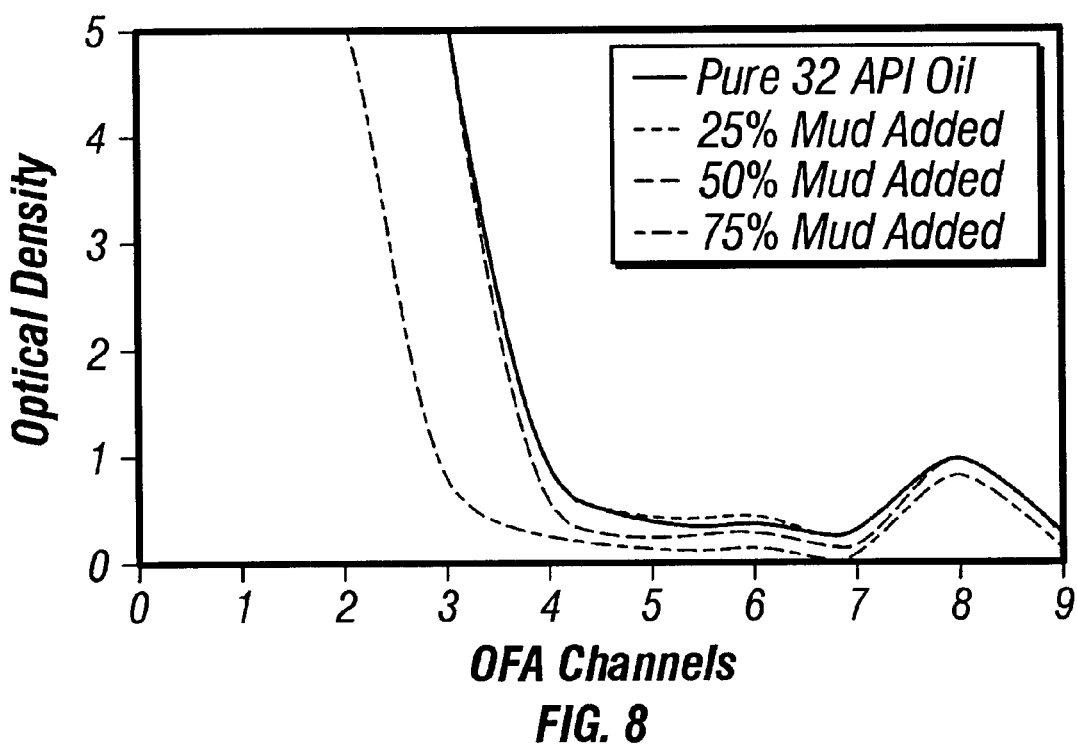
FIG. 8 is a plot of the optical density response for mixtures of synthetic oil-base mud and 32° API oil.

Results for the 32° API oil are shown in FIG. 8. Decreasing amounts of synthetic oil-base mud in the mixture corresponded to increased optical density values on channels 3–9. Responses similar to those in FIG. 8 were observed earlier for oil-base mud filtrates (FIG. 6) and for hydrocarbons of API gravity less than 40° (FIG. 3); the latter have a higher optical density than do oil-based filtrates. For the 41° API oil (not shown), the overall effect of decreasing the percentage mud was to increase optical density in all channels. Fluid coloration (FCOL) increased after the mixture became primarily hydrocarbon.

Because of the differences in the composition of various crude oils, their characteristic absorbency may differ from the oil used for analysis. Therefore, it is recommended that both the crude and mud filtrate characteristic optical density data be determined prior to sampling if possible. The measured data can be used to estimate the actual API gravity of the crude oil. Experience has shown that surface measurements of optical density are not significantly different from the downhole data even though some of the volatile hydrocarbon components may have evolved from the sample. The lighter hydrocarbon molecular components are not the primary absorbers of light spectra in the selected OFA channels in the visible region (up to approximately 750 nm) and the infrared region.

Figure 9:
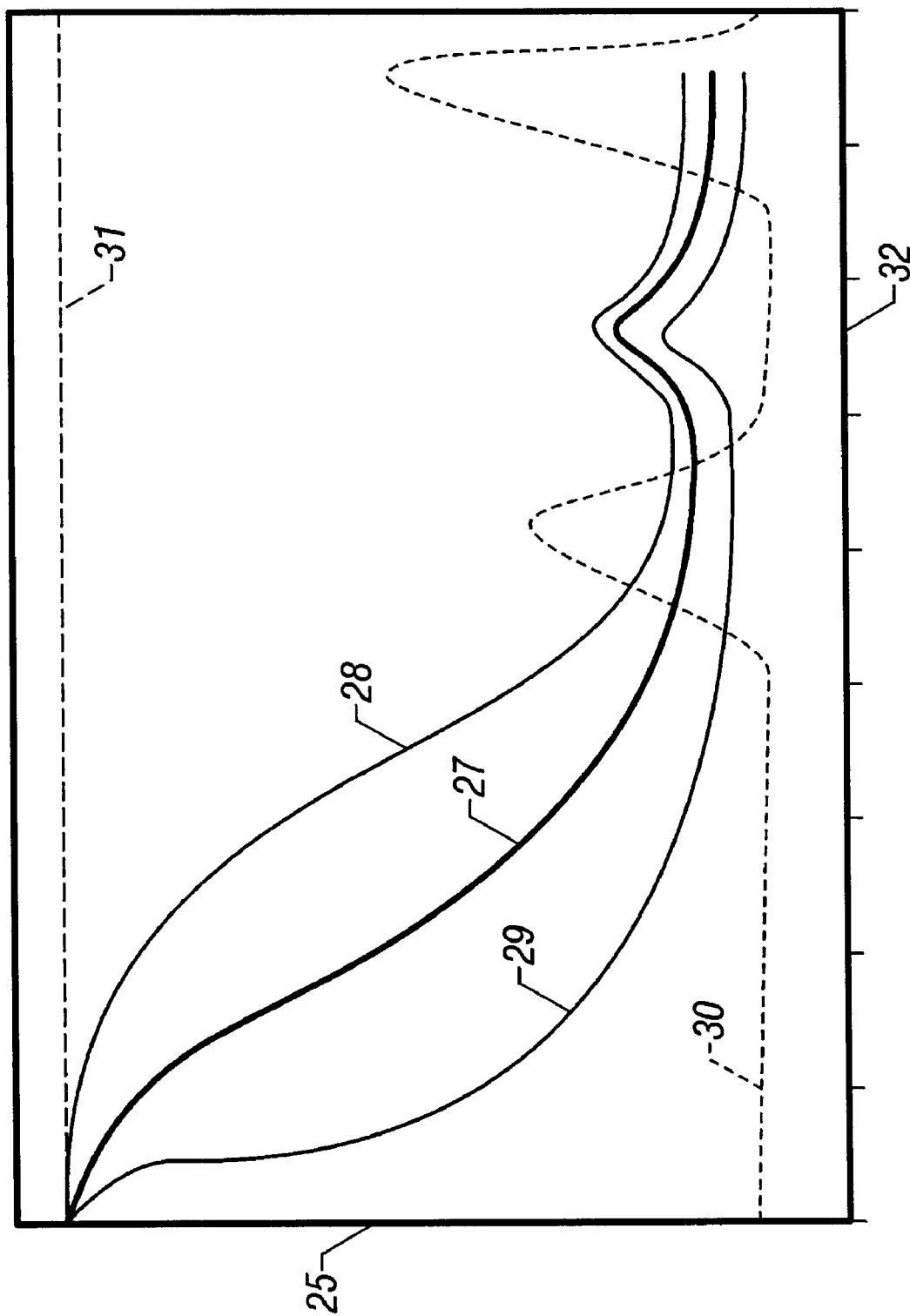
FIG. 9 is a plot of the measured fluid optical density response during the operation of the present invention.
Figure 10:
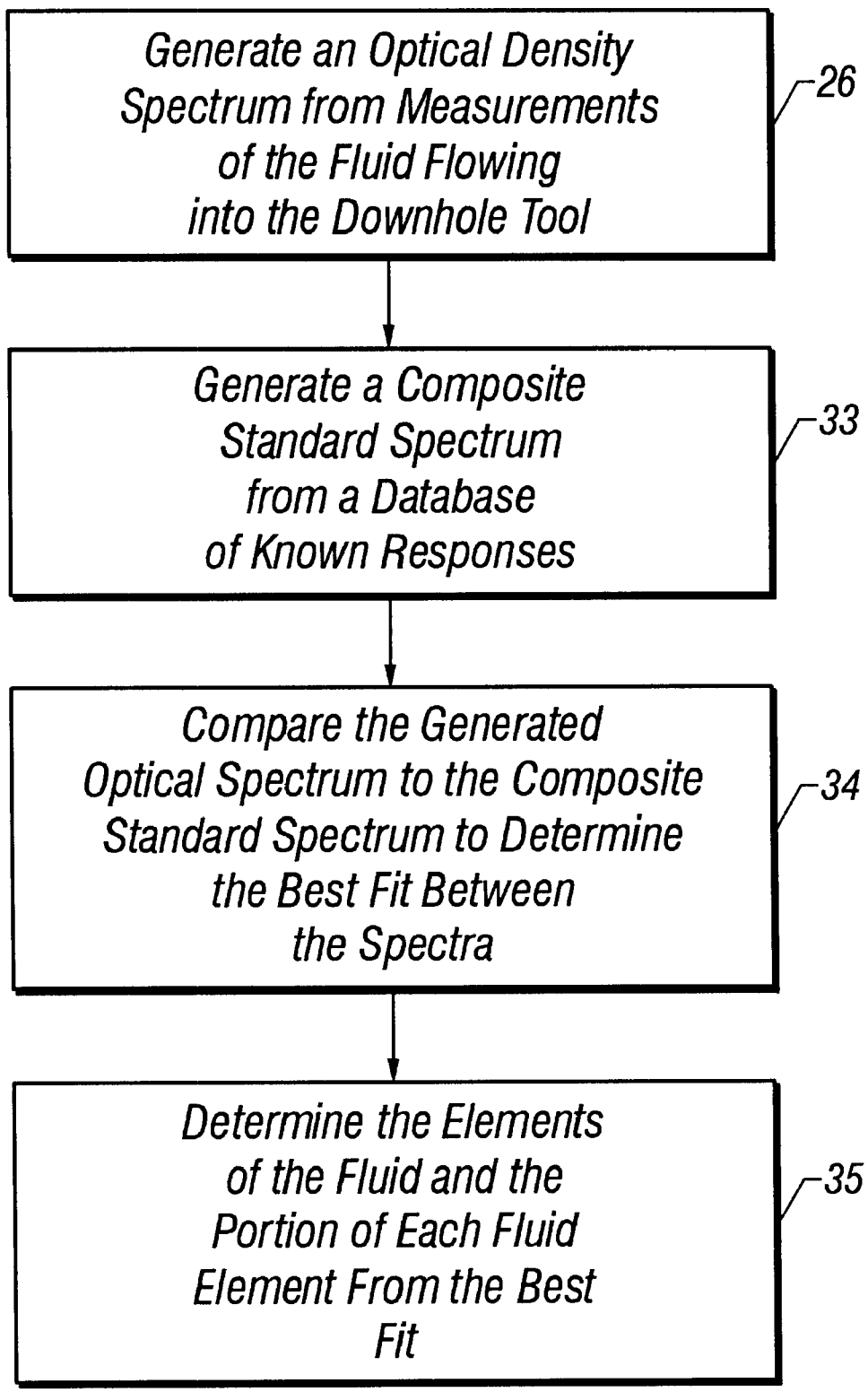
FIG. 10 is a flow chart of the steps of the present invention.

The present invention is now described with reference to FIGS. 9 and 10. The method evaluates the volumetric fraction of a fluid having multiple component mixtures which can include: 1) highly absorbing materials called solids; 2) water; 3) mud filtrates; and 4) formation hydrocarbons called oil-1 and oil-2. Highly absorbing materials and water are generally defined and distinguished from the formation hydrocarbons. The major task is to differentiate oil-base mud filtrates from the formation hydrocarbons. The formation-testing tool 1 attaches to the formation wall and begins the process of drawing fluid from the formation into the tool. The fluid travels through the flowline 13 and passes the OFA module 6. The OFA generates, in step 26 of FIG. 10, the absorption spectrum 27, shown in FIG. 9, of the fluid by passing light through the fluid as it passes the OFA sensor. The generated spectrum is a summation of the hydrocarbon spectrum 28, the oil filtrate spectrum 29, the water spectrum 30, and the high absorbing spectrum 31 The OFA sensors measure the optical density 25 of the fluid by detecting absorption wavelengths in the fluid. These wavelengths are distributed across a set of 10 channels 32. Each channel has a wavelength range of approximately 175 nanometers. This measured spectrum contains responses from materials that comprise the fluid.

At this point, it is necessary to determine the materials in the fluid. This procedure involves the construction of a composite standard spectrum, as indicated at step 33 in FIG. 10. This composite standard spectrum, also referred to herein simply as a "composite spectrum," is a spectrum of materials that may be in the fluid. The initial composite spectrum is generated from a set of inputs of possible fluid combinations. These inputs are the assumptions resulting from estimates of what materials are in the formation. These inputs include estimates of solids, water, filtrates and hydrocarbons. From the assumption above, a linear fraction of each of the optical components that correspond to each material can be summed to produce a composite spectrum.

The use of one or more formation hydrocarbon inputs (for example, oil-1 and oil-2) in the process depends on the information available at the start of the sampling operation. If the approximate oil gravity (degree API) in the zone of interest is known, the particular oil in the database closest to the known reservoir value can be input to the composite spectrum. This means that the solution will be for four-mixture components. If the formation hydrocarbon is unknown, then based on local experience, it is recommended to bracket the expected value by inputting higher and lower values (oil-1 and oil-2) into the composite spectrum. A field estimation of the formation hydrocarbon density is not possible until sufficient fluid has been produced from the formation. A process can produce spectra having various mixtures of the two oils (such as a spectrum where the hydrocarbon input is 70 percent of oil-1 and 30 percent of oil-2).

The next step 34 is to compare the measured and composite spectra. The comparison of the measured spectrum 27 and the composite spectrum uses a weighted least squares solution to perform spectral fitting on the measured optical spectrum. This spectral fitting technique requires that an assumption be made that the measured optical spectrum is a linear sum of the relative contributions of the individual components of oil, water and drilling fluids. If this is true, then the composite spectrum of selected fluids from the database of the optical spectral data can be linearly weighted and summed in an attempt to fit the measured optical spectrum 27. The weights are based on assumptions of the relative contributions of the individual components. This composite spectrum is then compared to the measured spectrum 27 to determine the best fit between the two spectra. Changes are then made in the fractional contribution of each standard until the composite spectrum matches the measured spectrum. This match will not be a perfect match as there can be variations in the spectrum due to temperature and pressure. The "fit" between the measured and composite spectra is tested at every sample and when the overall error is at a minimum the fitting process is stopped. The resulting composite spectrum contains known fractions of the elements in the formation fluid. A review of this spectrum can determine the portion of each element in the formation fluid 35. Various types of weighted regression programs are commercially available for this purpose.

In generating the composite spectrum, this embodiment of the invention allows for initial inputs of up to five components, including a mixture of two oils. The components normally included in the spectrum are: opaque material (solids), water, one drilling fluid and two specified API gravity oils. If the API gravity of the oil is known, the uncertainty of the calculation can be improved by selecting only the one proper API gravity oil. The ability to solve for different oils provides the capability of bracketing the estimated oil with a higher and lower API gravity oil. Once the initial computation provides an indication of what API gravity is being sampled, the gap between the two oils in the solution can be narrowed if needed to provide a more refined answer.

Figure 11:
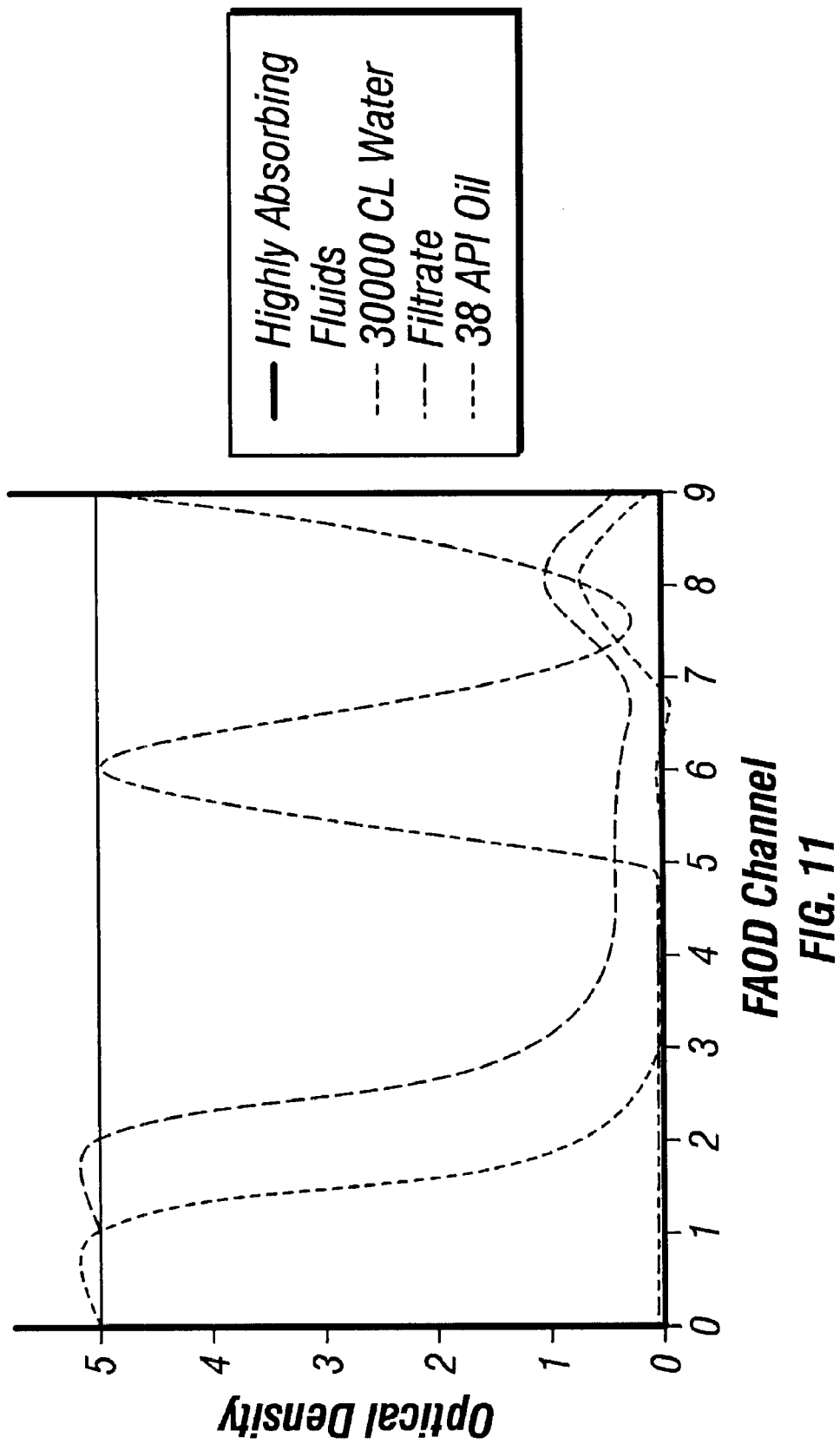
FIG. 11 is a plot of the interpretation inputs for a generated optical density spectrum.

FIG. 11 shows the typical interpretation inputs. The characterized inputs are from solids, oil, water and synthetic oil-base mud. The solver (a computer processor on a downhole tool or at the surface, for example) will be given 10 equations, one for each wavelength channel. In this case there will be 4 unknowns, one for each of the characterized expected formation outputs. The mathematical solution is over determined (more equations than unknowns) and the solver will iterate to an optimal solution through all 10 channel values.

Tests were performed to determine the reliability of the methods in the present invention. In the procedures of one test, normal fluid sampling operations start with a pretest to assure good hydraulic communication with the formation. Once communication has been established, the invaded mud filtrate near the wellbore is removed using the pumpout module. The flow through the tool is analyzed with the OFA module to monitor the oil and/or water production with time. Generally, a highly absorbing fluid composed partly of formation solids and mud particles initially blocks all transmitted light and maximum optical density measurements are recorded. The flow then cleans up to show water and/or oil flowing through the tool. This fluid may contain oil-base mud filtrate along with crude oil. With continued clean up operations, the optical density values in channels 3 through 7 of the OFA are monitored to determine when the fluid content has stabilized. With synthetic oil-base mud filtrates, this usually means that the optical density values decrease to low values before they begin to increase toward values reflecting increased volumes and density of the formation crude oil.

Real-Time Estimation of API Gravity by OFA

Figure 12A:
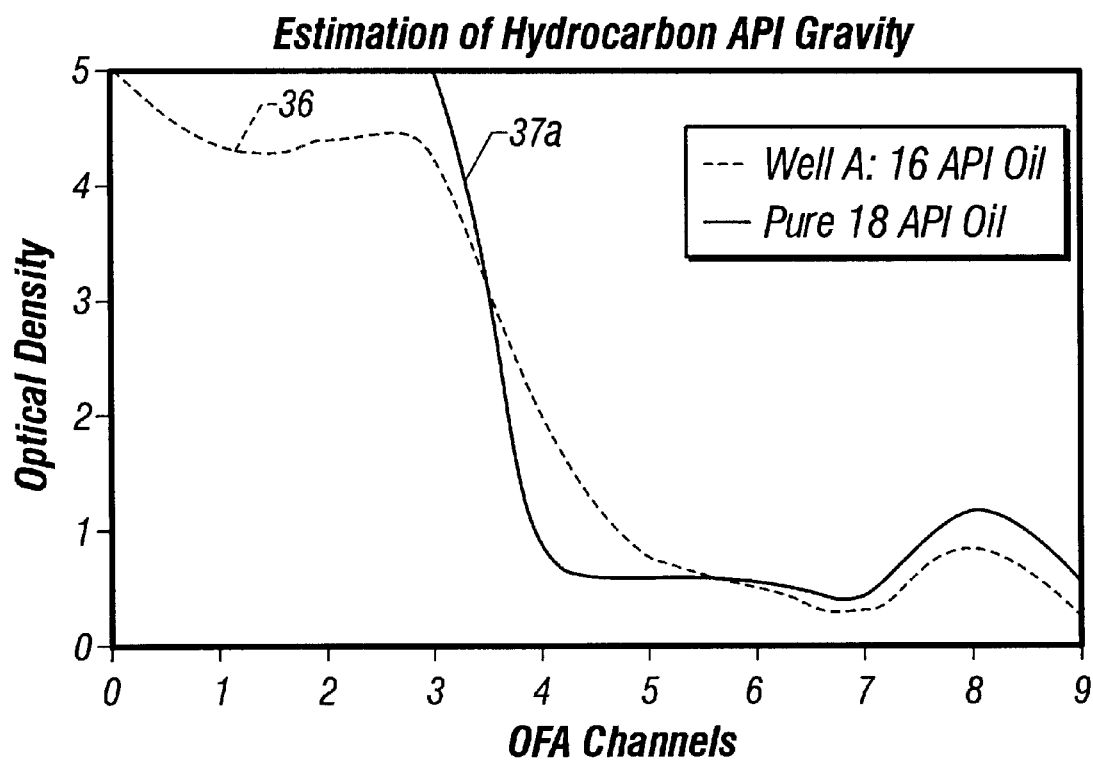
FIGS. 12(a)–12(c) are plots of field optical density measurements compared to known responses for estimating hydrocarbon API gravity.
Figure 12B:
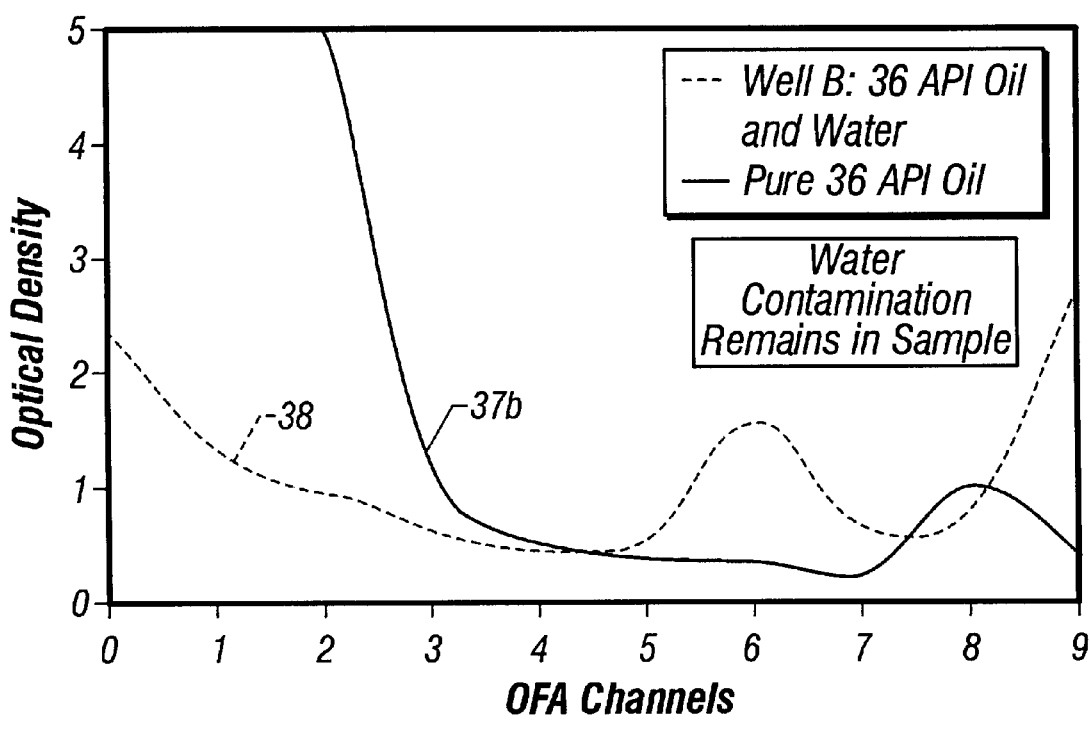
Figure 12C:
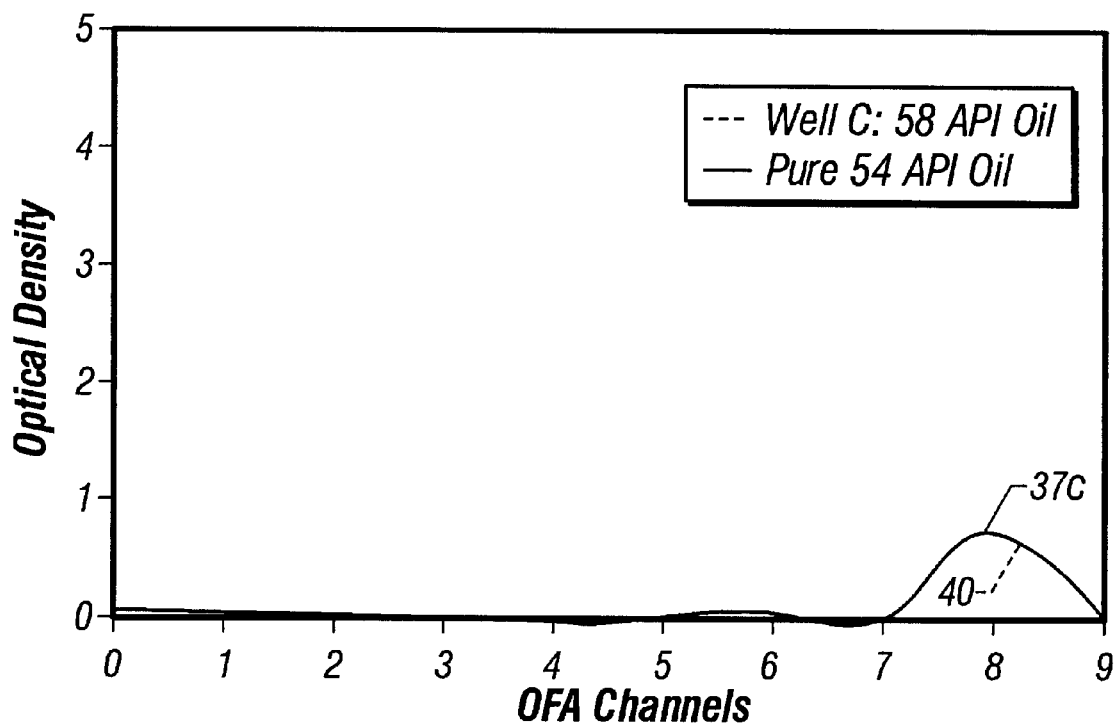

Real-time downhole optical density measurements were made and compared to the typical OFA responses of FIG. 3 so that API gravity can be estimated. As a check, the estimated oil gravity was compared with PVT laboratory measurements made on recovered fluid samples. Some of the results from this procedure are shown in FIGS. 12(*a–c*) for very heavy, medium and very light crude oils. Optical density responses shown by the dashed curves labeled as 36, 38, and 40 in FIGS. 12(*a–c*) were obtained from the OFA following a pump out period and just prior to sampling. Channels 3–9 were found to be the most useful for "matching" the field data 36, 38, and 40 to known base responses (the solid curves 37*a*, 37*b*, and 37*c* taken from FIG. 3 for estimation of oil gravity).

In the case of FIG. 12(*a*), the closest response to field data 36 is that of a heavy oil 37*a*. This was confirmed subsequently when the density of the recovered oil sample 36 was measured to be 16° API. The example 38 from a second well in FIG. 12(*b*) possesses "middle range" oil gravity by comparison of OFA responses 37*b* (channels 3–5 in this case). The peaks on channels 6 and 9 indicate that not all the water used in mud makeup was removed from the hydrocarbon sample during MDT pump out operation. Oil 38 recovered at the surface was measured at 36° API, and the sample chamber contained 4500 cc of oil and 3800 cc of water as predicted by the OFA "effective flow stream" model. There is little difficulty in distinguishing between water and hydrocarbons using optical density measurements. The example 40 shown in FIG. 12(*c*) very clearly comes from a well in which light hydrocarbons were flowing downhole. Oil gravity measured at the surface was about 58° API and compared quite favorably with the OFA database results 37*c* of 54° API.

Oil Sample in Synthetic Oil-Base Mud

Figure 13A:
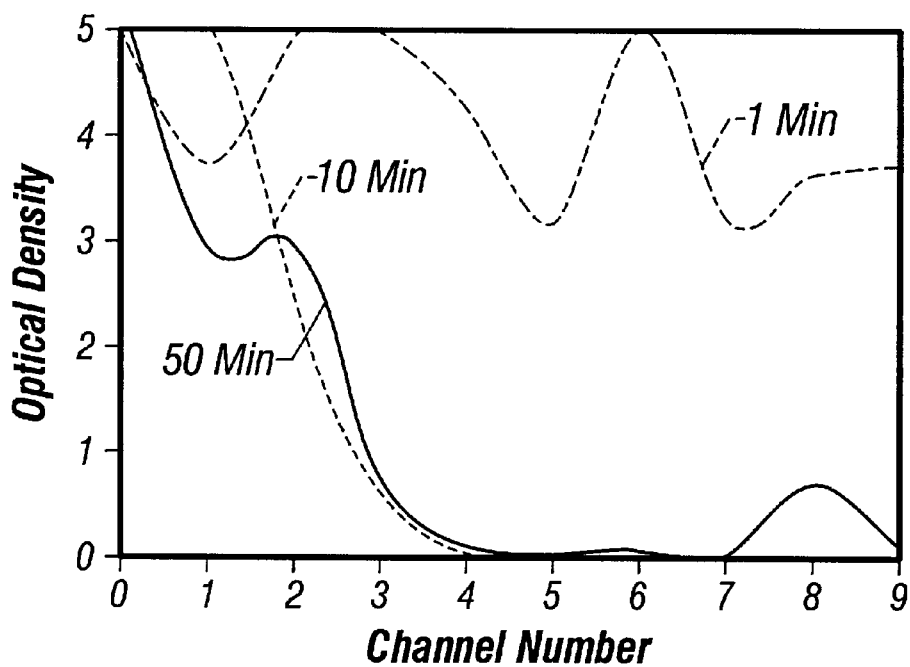
FIG. 13(a) is a plot of optical density measurements for a light hydrocarbon taken at 1 minute, 10 minutes, and 50 minutes.
Figure 13B:
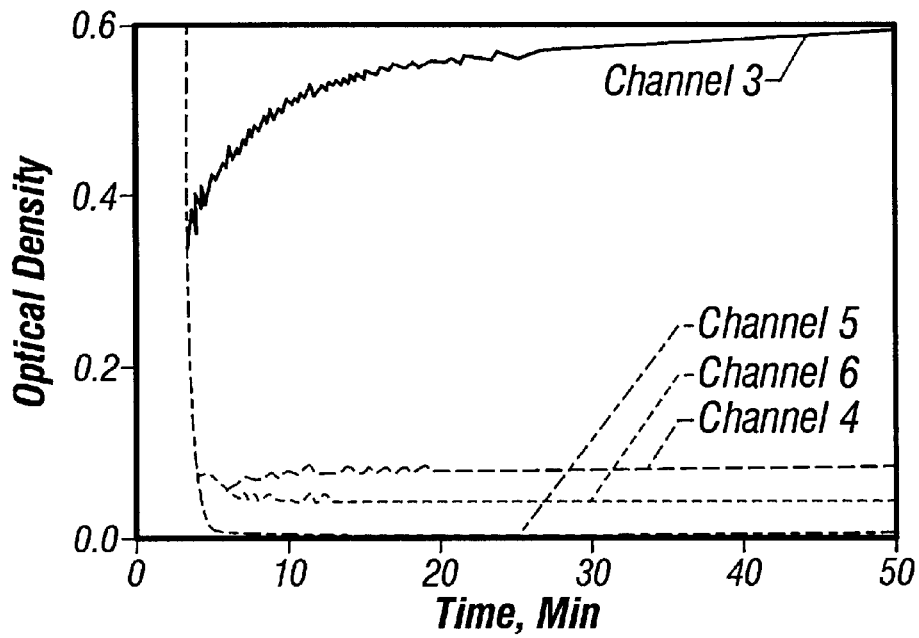
FIG. 13(b) is a plot of the optical density response versus time of the same light hydrocarbon of FIG. 13(a) for channels 3–6.

The example in FIGS. 13(*a*) and 13(*b*) was obtained in a well drilled with synthetic oil-base mud and illustrates the possibility of obtaining a light hydrocarbon fluid sample with very low mud contamination. The test compared optical density plotted at various intervals during the pump out operation. During this test, water contamination cleans up after less than 10 minutes of pumping, but contamination from base oil filtrate requires over 40 minutes to clean up. After 40 minutes of pumping fluid from the formation optical density values in channel 3 continue to increase; channels 4 and 5 increase slightly, while channel 6 becomes steady and even decreases somewhat. Little or no water is present in the fluid. After 50 minutes of clean up a hydrocarbon sample was pumped into a chamber held at wellbore hydrostatic pressure.

The optical density indicates a light oil gravity hydrocarbon (36°–40° API). Upon PVT lab analysis it was found that synthetic oil-base mud contamination in the sample chamber was very low (<5%). By utilizing real-time monitoring of specific optical density data (by waiting until channels 3–7 stabilized and channels 6 and 9 values were very small), a means of minimizing the sample contamination level was found. Specifically, further pumping is not expected to reduce the base oil contamination level in such miscible (OBM/oil sample) conditions.

The data depicted in FIGS. 13(*a*) and 13(*b*) is dynamic field data from a well in North America presented as optical density (OD) versus time. Channel 3 may be selected, for example, as the primary diagnostic channel for determining when it is desirable to collect a sample of the formation fluid flowing through the downhole tool. Other channels (0, 1, 2, and 4) or any other wavelengths can also be chosen, but the channel 3 response shown is a very typical response of a pumping sequence, especially for the lower OFA channels. For the upper channels or any other wavelengths, it varies only slightly (increasing or decreasing in value depending on the formation oil). The process may also include using the fluid coloration data.

With particular reference now to FIG. 13(*b*), the several stages for an oil-based mud system will now be described. In the beginning, stage 1 can be described as a debris-flowing stage where mud debris such as mud cake, or drilling mud is being pumped through the tool. Whenever solids travel through the OFA, they block light to all channels. This results in all channels having the maximum reading for OD since no light is being transmitted through the OFA. The maximum reading is generally anything over 3.

Once the fluid flow is substantially free of solids, the debris-flowing stage ends. The next stage is the removal of mud filtrate, which may be called the clean-up stage. Between the first two stages, generally there is a minimum OD that channel 3 reads, as indicated around 3-minutes on FIG. 13(*b*). During this mud removal process, the OD tends to increase gradually, almost in an exponential shape as the filtrate is slowly being minimized.

The third stage is the steady state flow condition. At this point, when the flow reaches steady state and the OD response is changing very little, it is a good time to take a quality fluid sample.

Knowledge gained from these three flow stages of the pumping sequence may be applied to help predict the type of crude oil standard spectra component(s) for input into the composite spectrum. The prediction can be obtained a number of ways: by looking for steady state flow response; by using the shape of the curves during any or all of the stages; and by using the time for the minimization of OD changes between stages 2 and 3.

The equation below can be used to estimate the approximate time for stabilized flow (third stage):

$$t_c = \beta\pi\phi(r_i-r_w)^3 \div (3Q(k_h/k_v)^{0.5}) + C$$

where t_c=time to reach stable flow
β=empirical constant
π=3.1416
φ=formation porosity
$r_i$=radius of invaded zone
$r_w$=radius of wellbore
Q=flow rate
$k_h$=horizontal permeability
$k_v$=vertical permeability
C=time at start of mud filtrate cleanup The mud filtrate decrease and the start of crude oil flow into the tool may be observed by monitoring the optical density response in the channels (such as channel 3). The slope of the optical density channel changes with time, and may be projected using a linear plot of OD versus time (or the derivative of OD versus time) to recognize the stabilized flow regime of crude oil through the OFA. The flow composition at this stage may be a mixture containing any combination of solids, water, mud filtrate and crude oil.

Since the exact properties of the crude oil are unknown, the upper and lower optical density bounds of the crude oil may be estimated from the data obtained during the stabilized flow period. The lower limit is basically the measured formation fluid OD spectrum at stabilized flow conditions since a formation hydrocarbon generally shows more spectral absorption than the other fluid components. The upper limit for the spectral response of the unknown crude is obtained from the projected behavior of the measured formation fluid spectrum from the stabilized flow period to infinite time.

At this point, the measured formation fluid spectrum data is entered into the weighted linear regression model to determine the fluid composition in terms of five components—solids, water, mud filtrate, and two known crude oils which bound the estimated formation crude oil. The resulting fluid composition determines the sample contamination level. Variations of this technique, such as using more or less optical density channels or ratios of the optical density data, are considered to be options of this invention. This model can be applied in real time.

Estimating Oil Sample Contamination in Synthetic Oil-Base Mud

Monitoring the stabilization of fluid flow conditions during the sampling operation, by using the optical density data channels, will improve the quality of the fluid sample, but it will not provide a direct measurement of the actual sample contamination level. The fluid flow regime into the probe, even under stable conditions, can include a significant vertical component from the borehole-invaded zone, which contains mud filtrate contamination.

Figure 14:
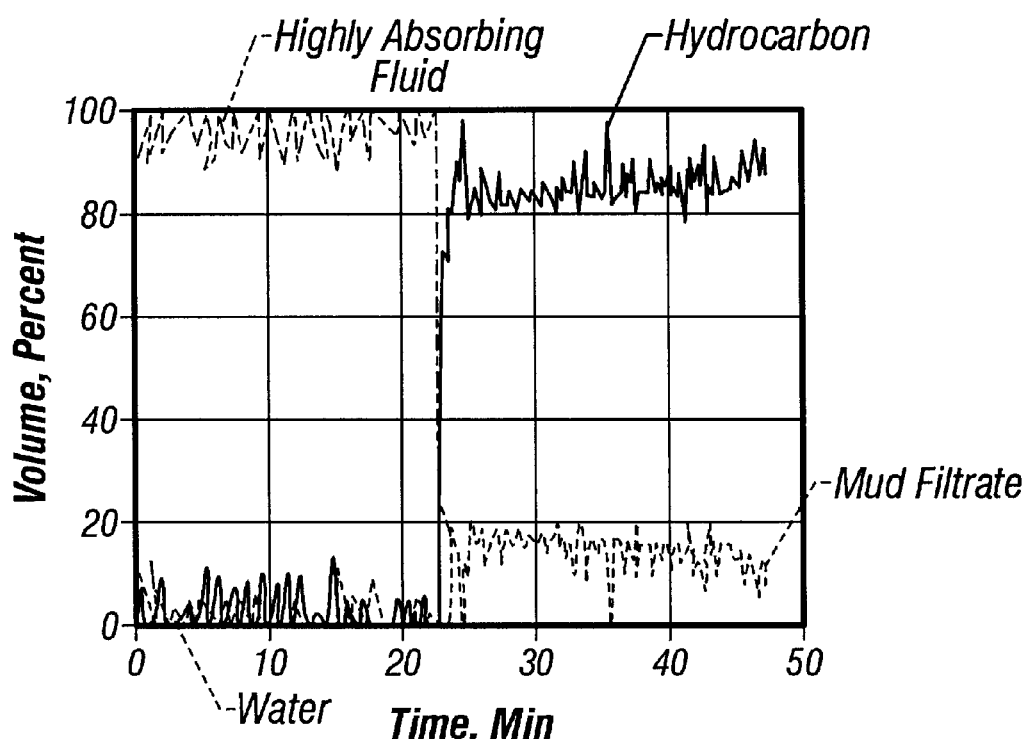
FIG. 14 is a plot representing the synthetic oil-base mud contamination in a hydrocarbon sample.

In the example shown in FIG. 14, the synthetic oil-base mud filtrate contamination was predicted as a function of time. The results showed the estimated volumetric content of the flowing fluid presented in a five component model: solids (any opaque material) water, mud filtrate, and formation hydrocarbon (oil-1 and oil-2). The estimated mud contamination decreases rapidly at about 23 minutes, but stabilizes at a near constant 15% level during most of the pumping operation. Continued pumping of fluid is not expected to change the contamination level significantly and illustrates the effect of the flow regime on the final sample quality. The predicted contamination level agreed very favorably with the results from the sample PVT analysis.

The methods of this invention provide significant advantages over the current art. The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of this invention, which is limited only by the following claims.

We claim:

1. A method for improving the quality of a formation fluid sample taken by a downhole tool, comprising the steps of:
   placing the downhole tool in fluid communication with the formation;
   inducing fluid flow from the formation through the downhole tool;
   measuring the optical density of the formation fluid as it flows through the downhole tool to generate an optical density spectrum;
   determining the amount of contaminant in the sample from the generated optical density spectrum; and
   determining when to collect a sample of the formation fluid from the determined fluid flow characteristics.

2. The method of claim 1, wherein the generated optical density spectrum includes ten discrete measurement channels.

3. The method of claim 2, wherein one of the channels is chosen as a primary source for determining the fluid flow characteristics from the generated optical density spectrum.

4. The method of claim 2, wherein any combination of channels is chosen as a primary source for determining the fluid flow characteristics from the generated optical density spectrum.

5. The method of claim 2, wherein any wavelength is chosen as a primary source for determining the fluid flow characteristics from the generated optical density spectrum.

6. The method of claim 1, wherein the determined fluid flow characteristics include the identification of a plurality of stages during the flow of the formation fluid through the downhole tool.

7. The method of claim 6, wherein the plurality of stages comprises a debris-flowing stage, a clean-up stage, and a steady-state flow stage.

8. The method of claim 7, wherein the debris-flowing stage is characterized by maximum optical density readings.

9. The method of claim 7, wherein the start of the clean-up stage is characterized by a minimum optical density reading.

10. The method of claim 7, wherein the steady-state flow stage follows a period of gradual increase in optical density readings for some channels and is characterized by substantially constant optical density readings.

11. The method of claim 7, wherein the steady-state flow stage follows a period of gradual increase in optical density readings for some wavelengths and is characterized by substantially constant optical density readings.

12. The method of claim 7, wherein the steady-state flow stage follows a period of decrease in optical density readings in some channels and is characterized by substantially constant optical density readings.

13. The method of claim 7, wherein the steady-state flow stage follows a period of decrease in optical density readings in some wavelengths and is characterized by substantially constant optical density readings.

14. The method of claim 7, wherein the generated optical density spectrum includes ten discrete measurement channels, and one of the channels is chosen as a primary source of the optical density readings for characterizing the three stages.

15. The method of claim 7, wherein the generated optical density spectrum includes ten discrete measurement channels, and a combination of the channels is chosen as a primary source of the optical density readings for characterizing the three stages.

16. The method of claim 7, wherein the formation fluid sample is collected during the steady-state flow stage.

17. A method for determining when to collect a sample from formation fluid sample flowing through a downhole tool, comprising the steps of:

measuring the optical density of the formation fluid as it flows through the downhole tool to generate an optical density spectrum;

determining the amount of contaminant in the sample from the generated optical density spectrum; and determining when to collect a sample of the formation fluid from the determined fluid flow characteristics.

18. The method of claim 17, wherein the determined fluid flow characteristics include the identification of a plurality of stages, comprising a debris-flowing stage, a clean-up stage, and a steady-state flow stage.

19. The method of claim 18, wherein the debris-flowing stage is characterized by maximum optical density readings.

20. The method of claim 18, wherein the start of the clean-up stage is characterized by a minimum optical density reading.

21. The method of claim 18, wherein the steady-state flow stage follows a period of gradual increase in optical density readings, and is characterized by substantially constant optical density readings.

22. The method of claim 18, wherein the generated optical density spectrum includes ten discrete measurement channels, and one of the channels is chosen as a primary source of the optical density readings for characterizing the stages.

23. The method of claim 22, wherein the formation fluid sample is collected during the steady-state flow stage.

24. The method of claim 17, further comprising the steps of:

establishing a composite optical density spectrum from individual standard spectra components; and comparing the generated spectrum with the composite spectrum to determine the composition of the formation fluid.

25. The method of claim 24, wherein the spectra comparison step includes determining the best fit between the generated spectrum and the composite spectrum by adjusting the fractal portions of the individual standard spectra components in the composite spectrum.

26. The method of claim 25, further comprising the steps of:

evaluating the determined best fit; and adjusting the individual standard spectra components that make up the composite spectrum until an acceptable best fit is obtained.

27. The method of claim 24, wherein the composite optical density spectrum pertains to a multi-phase fluid comprising a mixture of a crude oil, water and gas in the formation fluid, and the composite optical density spectrum is established by evaluating the determined fluid flow characteristics.

28. The method of claim 27, wherein the determined fluid flow characteristics include the identification of a plurality of stages, comprising a debris-flowing stage, a clean-up stage, and a steady-state flow stage.

29. The method of claim 28, wherein the formation fluid comprises crude oil, and wherein the composite optical density spectrum includes one individual standard spectra component believed to have greater optical density values than the crude oil in the formation fluid and one individual standard spectra component believed to have lower optical density values that the crude oil in the formation fluid.

30. The method of claim 29, wherein the greater-density component and the lower-density component are determined from the steady-state flow stage.

31. The method of claim 30, wherein the lower-density component is determined by selecting an individual standard spectra component having an optical density spectrum that approximates the generated optical density spectrum from the formation fluid.

32. The method of claim 30, wherein the upper-density component is determined by projecting the behavior of the steady-state flow stage to infinity.

* * * * *